US005698327A

United States Patent [19]
Persello

[11] Patent Number: 5,698,327
[45] Date of Patent: Dec. 16, 1997

[54] ZINC/DENTIFRICE-COMPATIBLE SILICA PARTICULATES

[75] Inventor: Jacques Persello, Montluel, France

[73] Assignee: Rhone-Poulenc Chimie, Courbevoie Cedex, France

[21] Appl. No.: 310,773

[22] Filed: Sep. 27, 1994

Related U.S. Application Data

[62] Division of Ser. No. 353,528, May 18, 1989, Pat. No. 5,413,844.

[30] Foreign Application Priority Data

Jun. 1, 1988 [FR] France ................................ 88 07279

[51] Int. Cl.⁶ ........................................................ A61K 7/16
[52] U.S. Cl. .......................... 428/404; 428/403; 428/406; 424/52; 424/57
[58] Field of Search ................................ 428/403, 404, 428/406; 424/52, 57

[56] References Cited

U.S. PATENT DOCUMENTS

| | | |
|---|---|---|
| 3,070,426 | 12/1962 | Winyall . |
| 3,794,712 | 2/1974 | Aboutbout et al. . |
| 3,800,031 | 3/1974 | Sale et al. . |
| 3,803,046 | 4/1974 | Winyall et al. . |
| 3,860,682 | 1/1975 | Reinhardt et al. . |
| 3,934,002 | 1/1976 | Haefele . |
| 3,963,512 | 6/1976 | Swift et al. . |
| 4,049,781 | 9/1977 | Acker et al. . |
| 4,076,549 | 2/1978 | Wason . |
| 4,216,113 | 8/1980 | Winyall . |
| 4,340,583 | 7/1982 | Wason . |
| 4,422,880 | 12/1983 | Wason et al. . |
| 4,508,607 | 4/1985 | Winyall . |
| 4,562,066 | 12/1985 | Hayes et al. . |
| 4,676,964 | 6/1987 | Seki et al. . |
| 4,704,425 | 11/1987 | Lagarde et al. . |
| 4,708,859 | 11/1987 | Chevallier . |
| 4,842,838 | 6/1989 | Chevallier . |
| 4,973,462 | 11/1990 | Akira et al. . |
| 5,124,143 | 6/1992 | Muhlemann et al. . |

FOREIGN PATENT DOCUMENTS

| | | |
|---|---|---|
| 0046057 | 2/1982 | European Pat. Off. . |
| 0 407 262 | 1/1991 | European Pat. Off. . |
| 710015 | 6/1954 | United Kingdom . |
| 719918 | 12/1954 | United Kingdom . |

OTHER PUBLICATIONS

"Perry's Chemical Engineers' Handbook", Green & Maloney, 6th Edition, pp. 18.1–18.3, 18.50, McGraw Hill, NY, NY (1984).

"Pigment Handbook: vol. 1: Properties and Economics Second Edition", Wason, Satish, pp. 139–159, John Wiley & Sons (1988).

Wason, S. K., "Cosmetic Properties and Structure of Fine-Particle Synthetic Precipitated Silicas", *J. Soc. Cosmet. Chem.*, vol. 29, pp. 497–521 (Aug., 1978).

*Primary Examiner*—Kathleen Choi
*Attorney, Agent, or Firm*—Burns, Doane, Swecker & Mathis, L.L.P.

[57] ABSTRACT

Zinc-compatible silica particulates, useful for the formulation of a wide variety of improved dentifrice compositions, have an effective compatibilizing amount of zinc values chemically bonded to surface area sites of the particles.

23 Claims, No Drawings

ZINC/DENTIFRICE-COMPATIBLE SILICA PARTICULATES

This application is a divisional of application Ser. No. 07/353,528, filed May 18, 1989, now U.S. Pat. No. 5,413,844.

BACKGROUND OF THE INVENTION

1. Field of the Invention

The present invention relates to novel zinc-compatible silica particulates, to a process for the preparation thereof, and to the formulation of improved dentifrice compositions therefrom, notably dentifrice compositions containing zinc values.

2. Description of the Prior Art

It is known to this art that silica is a particularly useful component in dentifrice compositions. It serves a variety of functions in such dentifrice compositions.

It serves primarily as an abrasive and polishing agent by mechanically assisting in the removal of dental plaque.

It can also serve as a thickening agent to confer predetermined rheological properties to the dentifrice, as well as an optical agent to impart desired coloration thereto.

It too is known to this art that dentifrices contain various other ingredients, in particular for the prevention of caries, to reduce the formation of dental plaque or the deposition of tartar onto the teeth. Among these other ingredients or agents, zinc is specifically representative. Other constituents are also included, such as fluorides, phosphates, pyrophosphates, polyphosphates, polyphosphonates, guanidines, in particular the bis-biguanidines, and, most typically, chlorohexidine. The various dentifrice compositions may also contain such additives as flavors, perfumes, and the like.

The presence of these agents in a dentifrice composition presents the serious problem of their compatibility, or, more correctly, their incompatibility with silica. Indeed, principally due to its absorbent properties, the silica tends to react with a number of such added agents, notably zinc values, to an extent that they are not longer available to elicit their desired therapeutic or cosmetic effects described above.

SUMMARY OF THE INVENTION

Accordingly, a major object of the present invention is the provision of novel dentifrice-compatible silica particulates, notably zinc-compatible silica particulates.

Another object of this invention is the provision of a process for the preparation of such dentifrice/zinc-compatible silica particulates.

Briefly, it has now been discovered that the compatibility properties of silica depend on the surface chemistry of the particulates. More especially, it has now unexpectedly and surprisingly been determined that the presence of zinc values on the surface area of the silica particles, affixed thereto by a specific treatment according to this invention, imparts zinc- and other compatibility to said treated silica particulates.

Thus, the novel silica particulates of the present invention are characterized in that zinc values are borne on the surface area thereof, said zinc values being chemically bonded to the external face surfaces thereof.

This invention also features a process for the preparation of such zinc-compatible silica particulates. The subject process comprises treating silica particles, either during a stage of or subsequent to the synthesis thereof, with a zincate, and either conjointly with or after said zincate treatment, further treating the zincated particles with an acid medium.

Lastly, the present invention also features improved dentifrice compositions based on the aforedescribed zinc-compatible novel silica particulates.

DETAILED DESCRIPTION OF THE PREFERRED EMBODIMENTS OF THE INVENTION

More particularly according to the present invention, the subject novel silica particulates have an especially high compatibility with zinc, in particular an at least 50% compatibility.

As above indicated, the essential property of the silica of the invention is its surface chemistry. These novel silica particulates contain zinc values on the external face surfaces thereof, and the zinc is bonded chemically to such surface sites.

The existence of the chemical bonding may be determined by the behavior of the silica when placed into an aqueous suspension, for example in water, at pH 7. In this case, no desorption of zinc is detected, or only a negligible desorption occurs due to trace amounts of zinc not chemically bonded; these trace amounts may result by reason of using a lesser purity of starting silica.

Without intending to be limited to any particular theory, it is reasoned that such chemical bonding is likely of the Si—O—Zn type, and more particularly of the following type at the face surface of the silica particulates:

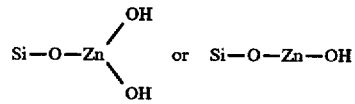

Finally, it will also be appreciated that the zinc atoms directly participate in the Si—O—Zn bond according to the invention, in contrast to certain silicas of the prior art, the surfaces of which may indeed include zinc, but in the form of compounds such as zinc sulfate, for example, which are not chemically bonded thereto. Rather, such compounds are simply reversibly adsorbed thereon.

As above indicated, the silica particulates of the invention have an at least 50% compatibility with zinc. In a preferred embodiment of the invention, this compatibility may be at least 80% and even at least 95%. The compatibility is determined by a test more fully described below.

The zinc content of the silica particulates may vary as a function of the specific surface of the silica and also of the application. Generally, it is preferred to limit this amount to 10% by weight of Zn relative to the $SiO_2$. This limit may be reduced to 5% Zn. In a preferred embodiment of the invention, such amount is at most 1% and, even more preferably, at most 0.5%.

A novel and particularly advantageous attribute of the silica particulates of the invention is that, in contrast to the prior art, such silica may have a significantly enhanced compatibility with zinc, while containing a lesser amount of this element. Thus, the aforementioned compatibility of 50% may be attained in a silica according to the invention having a maximum zinc content of 5%.

In addition to the characteristics of surface chemistry described above, which dictate compatibility, the silica particulates of the invention also have physical properties which render them perfectly suited for incorporation in dentifrice compositions. These properties, of a structural type, are described below.

Generally, the BET surface area of the silica particulates of the invention ranges from 40 to 600 m²/g. Their CTAB surface area typically ranges from 40 to 400 m²/g.

The BET surface area is determined by the Brunauer-Emmet-Teller method described in *Journal of the American Chemical Society*, Vol. 60, p. 309 (February 1938) and according to the standard NF T45 007 (5.11).

The CTAB surface area is the external surface determined by the standard NF T45 007 (5.12).

The silica particulates of the invention may comprise any of the three types typically included in dentifrice compositions.

Thus, the silica particulates of the invention may be of the abrasive type. These typically have a BET surface area ranging from 40 to 300 m²/g. In this case, the CTAB surface area ranges from 40 to 100 m²/g.

The silica particulates of the invention may also be of the thickening type. These typically have a BET surface area ranging from 120 to 450 m²/g and preferably from 120 to 300 m²/g. And in this case the CTAB surface area typically ranges from 120 to 400 m²/g.

Finally, a third type of silica particulates of the invention may be bifunctional. These latter particulates typically have a BET surface area ranging from.80 to 200 m²/g. Their CTAB surface area typically ranges from 80 to 200 m²/g.

The silica particulates of the invention may advantageously have an oil uptake ranging from 80 to 500 cm³/100 g, determined according to the standard NFT 30-022 (March 1953), using dibutyl phthalate.

More particularly, such oil uptake (absorption) ranges from 100 to 140 cm³/100 g for the abrasive silica, 200 to 400 cm³/100 g for the thickening silica and 100 to 300 cm²/100 g for the bifunctional silica.

Furthermore, in light of their intended incorporation in dentifrice compositions, the silica particulates of the invention preferably have a particle size ranging from 1 to 10 μm.

The pH of the subject silica particulates, measured according to the standard NFT 45-007, typically ranges from 6 to 10.

Their apparent density typically ranges from 0.01 to 0.6.

Finally, the silica particulates of the invention preferably have a refractive index ranging from 1.440 to 1.465.

In a preferred embodiment of the invention, the silica particulates are of precipitated silica type.

The process for the preparation of the silica according to the invention will now be described.

The process comprises subjecting the starting material silica to two treatments, first by a zincate, and secondly by an acid. These two treatments may be carried out consecutively or simultaneously.

By "zincates" are intended those compounds containing the anions $ZnO_{22}-$, $HZnO_2-$, $Zn_2O_4{}^4-$ or $ZnO_4{}^6-$.

Preferably, the alkali metal zincates are employed and, even more preferably, sodium zincate.

These zincates may be prepared by reacting alkaline solutions with zinc or a zinc oxide.

In general, the zincate treatment is carried out by contacting the silica or a silica suspension with a zincate, typically in the form of a solution thereof.

The acid treatment is advantageously carried out by passing an acid solution over the silica, or by adding such acid solution to a suspension containing the silica.

In the latter case, an amount of acid solution is added such that the pH of the suspension after the treatment, i.e., after the addition of the solution, will have a value not less than 7.

This acid solution may be, for example, an aqueous solution of an inorganic acid, such as of nitric, sulfuric, hydrochloric, or carbonic acid.

However, this acid solution may also be a solution of an organic acid. It will be appreciated that the acid should not form complexes with zinc.

The aforesaid preparative process will now be described in greater detail.

It should first be noted that the treatments may be conducted either during the preparation of the silica itself, or on silica particulates that have previously been prepared.

The starting silica to be treated according to the invention may be prepared by any known technique. It may be precipitated silica produced by a process of the type comprising reacting a silicate with an acid agent, which results in the formation of a silica suspension or gel.

It will be appreciated that any known operation may be utilized to produce such suspension or gel (the addition of acid to the base of a vessel containing a silicate, the simultaneous total or partial addition of the acid and the silicate to the base of a vessel containing water or a silicate suspension, aging, etc.), the selection essentially being made as a function of the physical properties of the silica sought to be produced.

This is followed by the separation of the silica from the reaction medium by any known means, for example by vacuum or press filtering.

A silica cake is obtained in this manner, which is then washed, if necessary.

This filter cake, or suspension if disintegrated, is dried by any known means, in particular by atomization. The dried material is ground, if necessary, to obtain the desired grain size distribution.

According to the principal characteristic of the process according to the invention, the silica is treated with a zincate, which treatment may be carried out during any of the stages of the preparative process described above.

The zincate may be introduced into the suspension prior to the filtering step, or into the silica gel itself. However, if a suspension is produced, it is preferred to introduce the zincate after the separation/filtration stage.

In this case, the zincate is introduced into the cake resulting from the separation, or, more typically, into the suspension obtained after the disintegration of the cake.

The acid treatment may be carried out by the addition of an acid solution to the suspension prior to filtering, or to the gel, either simultaneously with or subsequent to the zincate treatment. Here again, however, it may be carried out after the separation, either on the cake or the disintegrated cake, by passing the acid solution over the cake or by adding an acid solution to a suspension of disintegrated material. Similarly, the acid treatment may be carried out either simultaneously with or subsequent to the zincate treatment.

It may also be advantageous to age the silica after the above treatments.

This aging step is typically carried out at a temperature of from 60° to 100° C. Of course, this aging step may be conducted as a function of the stage at which the zincate treatment is carried out. Accordingly, the aging is of either the suspension or gel directly produced by the precipitation reaction, or of the disintegrated filter cake, if the zincate treatment was carried out on the silica obtained by filtration.

In the case of a previously prepared silica or of a silica prepared by other than precipitation technique, the afore-described treatments may be used without any fundamental change.

These treatments are typically carried out by resuspending the silica and adding the zincate and the acid solution to the resulting suspension, as described above.

After processing, the treated silica may be washed, for example with deionized water, and then dried.

Generally, the washing process may be carried out on the cake obtained by filtering the aforesaid suspensions, whereupon the cake is disintegrated for subsequent drying. Characteristically, the pH of the suspension is adjusted, whereby the pH of the finished silica is determined.

The processes described above employ a zincate prepared prior to the treatment of the silica.

However, it is also within the scope of the present invention to prepare the zincate "in situ". In this case, instead of carrying out the treatment with a zincate, such as described above, the silica is treated with a mixture containing a zinc oxide, a silicate and a base, for example an alkali or alkaline earth metal hydroxide, or ammonium hydroxide.

An acid treatment of the aforementioned type is then carried out.

Another embodiment of the process of the invention relates to the preparation of silica particulates compatible with the guanidines and also with other compounds, such as fluorine and the phosphates.

This embodiment entails adequately washing the silica after the treatment. This washing is typically carried out on the cake obtained by the filtration of the above suspensions, until a filtrate is produced having a conductivity of greater than 2,000 microsiemens/cm, more preferably greater than 1,000 microsiemens/cm.

This invention also features dentifrice compositions containing the above silica particulates, produced by the afore-described zincate/acid treatment.

The amount of novel silica particulates incorporated into the dentifrice compositions according to this invention may vary over wide limits; typically, it ranges from 5 to 35% by weight.

The silica particulates of the invention are particularly suitable for incorporation in dentifrice compositions containing at least one of the following active agents: fluorides, phosphates, polyphosphates, pyrophosphates and polyphosphonates, zinc and the guanidines.

The amount of fluorine compounds incorporated is typically such as to provide a fluorine concentration of 0.01% to 1% by weight, preferably from 0.1% to 0.5% by weight of the dentifrice composition. Exemplary such fluorine compounds include the salts of monofluorophosphoric acid, and specifically those of sodium, potassium, lithium, calcium, aluminum and ammonium, mono- and difluorophosphate, as well as fluorides containing ionically bound fluorine, particularly the alkaline fluorides, such as sodium, potassium, lithium and ammonium fluoride, stannous fluoride, manganese fluoride, zirconium fluoride, and aluminum fluoride, together with the addition compounds of such fluorides, either with each other or with other fluorides, such as the potassium, sodium or manganese fluorides.

Other fluorides may also comprise the dentifrice compositions of the present invention, such as, for example, zinc fluoride, germanium fluoride, palladium fluoride, titanium fluoride, the alkali metal fluozirconates, for example of sodium or potassium, stannous fluozirconate, and the sodium or potassium fluoborates or fluosulfates.

The organic fluorides may also be incorporated, preferably the addition compounds of amines or long chain aminoacids with hydrogen fluoride, cetylamine fluoride, bis-(hydroxyethyl)aminopropyl-N-hydroxyethyloctadecylamine dihydrofluoride, octadecylamine fluoride and N,N',N'-tri-(polyoxyethylene)-N-hexadecylpropylenediamine dihydrofluoride.

The zinc values are typically incorporated in the form of a soluble salt thereof, in particular the citrate or sulfate.

Suitable anti-plaque agents are of the polyphosphate or polyphosphonate type, such as described in U.S. Pat. No. 3,934,002.

The dentifrice compositions of the invention may also contain a binder.

The principal binders are those selected from among:

(i) Cellulose derivatives: methylcellulose, hydroxyethylcellulose, sodium caroxymethylcellulose;

(ii) Mucilages: carraghenates, aliginates, agar—agar and geloses;

(iii) Gums: gum arabic or tragacanth gum, xanthan gum, Karaya gum;

(iv) Carboxyvinyl and acrylic polymers;

(v) Polyoxyethylene resins.

In addition to the silica particulates of the invention, the subject dentifrice compositions may also contain one or more other abrasive polishing agents, particularly selected from among:

(i) Calcium carbonate;

(ii) Magnesium carbonate;

(iii) Di- and tricalcic calcium phosphates;

(iv) Insoluble sodium metaphosphate;

(v) Calcium pyrophosphate;

(vi) Titanium dioxide (whitening agent);

(vii) Silicates;

(viii) Aluminas and silicoaluminates;

(ix) Zinc and tin oxides;

(x) Talc;

(xi) Kaolin.

The dentifrice compositions of the invention may also contain the usual detergents, humectants, flavoring agents, sweeteners, colorants and preservatives.

The principal detergents are selected from among:

(i) Sodium laurylsulfate;

(ii) Sodium laurylethersulfate and sodium laurylsulfoacetate;

(iii) Sodium dioctylsulfosuccinate;

(iv) Sodium laurylsarcosinate;

(v) Sodium ricinoleate;

(vi) Monoglyceride sulfates.

The principal humectants are preferably such polyalcohols as:

(i) Glycerol;

(ii) Sorbitol, typically a 70% solution in water;

(iii) Propylene glycol.

The principal aromatic agents (perfume) are selected from among the essences of anise, Chinese anise, mint, juniper berry, cinnamon, cloves and rose.

The principal sweetening agents are orthosulfobenzimides, saccharin and cyclamates.

The principal colorants depend upon the particular color desired and are selected from among:

(i) Red or rose coloration: amaranth, azorubin, catechu, cohenille, erythrosine, new coccine (PONCEAU 4R);

(ii) Green coloration: chlorophyll and chlorophyllin;

(iii) Yellow coloration: sun yellow (orange S) and quinoline yellow.

The principal preservatives are the parahydroxybenzoates, formol and derivatives thereof, hexetidine, quaternary ammonium salts, hexachlorophene, bromophene and hexamedine.

Lastly, the dentifrice compositions of the invention may also contain therapeutic agents, principally selected from among:

(i) Antiseptics and antibiotics;

(ii) Enzymes;

(iii) Oligocompounds and fluorine compounds described above.

In order to further illustrate the present invention and the advantages thereof, the following specific examples are given, it being understood that same are intended only as illustrative and in nowise limitative. In said specific examples, the compatibility of the silica particulates with various of the other constituents of the dentifrice compositions was measured according to the immediately following test procedures:

Measurement of compatibility with fluorides:

4 g silica were dispersed in 16 g of a 0.3% aqueous sodium fluoride (NaF) solution. The suspension was agitated at 37° C. for 24 hours. After centrifugation of the suspension at 2,000 rpm for 30 min, the supernatant was filtered over a 0.2 μm Millipore filter. The solution obtained in this manner was the test solution.

A reference solution was prepared in like manner, but excluding the silica.

Compatibility with fluorides was determined by the % of free fluoride measured using fluoride selective electrode (Orion). It was determined by the following relationship:

$$\% \text{ Compatibility} = \frac{\text{Concentration of F values in test solution (ppm)}}{\text{Concentration of F values in reference solution (ppm)}} \times 100$$

Measurement of compatibility with zinc 4 g silica were dispersed in 100 ml of a 0.06% aqueous solution of $ZnSO_4 \cdot 7H_2O$. A suspension having a pH stabilized at 7 in 15 min was produced by the addition of NaOH or $H_2SO_4$. The suspension was agitated for 24 hours at 37° C., then centrifuged at 2,000 rpm for 30 min.

The supernatant was filtered over a 0.2 μm Millipore filter and was the test solution.

A reference solution was prepared in the same fashion, but excluding the silica.

The concentration in free zinc of the two solutions was determined by atomic absorption (214 nm).

The compatibility was determined by the following relationship:

$$\% \text{ Compatibility} = \frac{\text{Concentration of Zn in test solution (ppm)}}{\text{Concentration of Zn in reference solution (ppm)}} \times 100$$

Measurement of compatibility with sodium and potassium pyrophosphates 4 g silica were dispersed in 16 g of a 1.5% aqueous suspension of sodium or potassium pyrophosphate. The suspension was agitated for 24 hours at 37° C., then centrifuged at 2,000 rpm for 30 min.

The supernatant was filtered over a 0.2 μm Millipore filter. 0.2 g of the solution was diluted in 100 ml water in a calibrated test tube and was the test solution.

A reference solution was prepared in like fashion, but excluding the silica.

The free pyrophosphate ion ($P_2O_7^{---}$) concentration of the two solutions was determined by ionic chromatography (DIONEX 2000i system), equipped with an integrator.

Compatibility was determined by the ratio of the peak areas of the peaks obtained by the chromatograms and corresponding to the retention time of the pyrophosphate of the test and the reference, according to the relationship:

$$\% \text{ Compatibility} = \frac{\text{Peak area of test solution}}{\text{Peak area of reference solution}} \times 100$$

Measurement of compatibility with chlorhexidine 4 g silica were dispersed in 16 g of an aqueous solution of chlorhexidine, having a 1% chlorhexidine digluconate concentration.

The suspension was agitated for 24 hours at 37° C.

The suspension was then centrifuged at 2,000 rpm for 30 min and the supernatant filtered on a 0.2 μm Millipore filter.

Subsequently, 0.5 ml of the solution filtered in this manner was diluted in 100 ml water in a calibrated test tube. This solution was the test solution.

A reference solution was prepared in like manner, but excluding the silica. An aqueous 1% solution of chlorhexidine digluconate was agitated for 24 hours at 37° C., then centrifuged at 2,000 rpm and the supernatant filtered on a 0.2 μm Millipore filter. 0.5 ml of the solution obtained in this manner was diluted in 100 ml water in a calibrated test tube.

The absorbance of the two solutions was then measured, at 254 nm, using a spectrophotometer (Uvikon 810/820).

The amount of free chlorhexidine constituted the % compatibility and was determined by the relationship:

$$\% \text{ Compatibility} = \frac{\text{Absorbance of test solution}}{\text{Absorbance of reference solution}} \times 100$$

EXAMPLE 1

This example describes the preparation of sodium zincate.

Into a double-walled glass reactor, equipped with an anchor stirrer for slow agitation, a bulb condenser and heated in an oil bath, 462 g of NaOH were added to 250 ml water at the base of the vessel.

The mixture was dissolved and heated.

At 65° C., 262 g ZnO were added. The temperature was increased further, under reflux.

At 160° C., after ½ hour, the suspension became clear and the dissolution was complete.

After ½ hour at reflux and 160° C., the suspension was permitted to cool. At 100° C., 575 ml water were added.

At 70° C., the solution salted out and the zincate could not be redissolved after 1 hour at 160° C.

The suspension was filtered at about 80° C.

The zincate produced had the following properties:

(a) Dry solids content=48%

(b) [Zn]=12.9%, i.e., [ZnO]=16.1% [Na$_2$O]=31.9%

(c) ZnO/Na$_2$O=0.39 molar (d) d=1.59.

EXAMPLE 2

Into a reactor equipped with a temperature and pH control system and a turbine agitation system, 6 l deionized water were introduced.

Following commencement of the agitation (300 rpm), the base of the reaction vessel was heated to 85° C.

When this temperature was attained, 8.5 l sodium silicate having a silica concentration of 120 g/l and a SiO$_2$/Na$_2$O ratio of 3.5 were added at a flow rate of 0.34 l/min simultaneously with 13.5 l of sulfuric acid at a concentration of 80 g/l. The acid flow rate was adjusted such as to maintain the pH in the reaction medium at a constant value of 8.0.

After 40 min of addition, the flow of silicate was discontinued and the addition of the acid continued until the pH of the reaction medium was stabilized at pH 4.

The medium was then aged for 15 min at this pH and at 85° C.

The mixture was then filtered and the wet filter cake washed with deionized water.

To the disintegrated cake, over 30 min, a solution containing 40 g sodium zincate prepared as in Example 1 and 60 g water were added. The pH was decreased to 8.3 by the addition of 20% hydrochloric acid and the reaction mixture was permitted to age for 15 min at 80° C.

The mixture was then filtered and the wet filter cake washed with deionized water, until the conductivity of the filtrate was less than 500 microsiemens.

The cake was then disintegrated, and the pH adjusted to 6 by the addition of acetic acid. A final wash was carried out using deionized water.

The product was then dried by atomization and ground on a forplex type grinder to obtain a grain size of 8 microns.

The physicochemical properties of the abrasive type silica particulates produced in this manner were as follows:

(i) BET surface area=100 m$^2$/g (ii) CTAB surface area=80 m$^2$/g (iii) DOP oil absorption=120 ml/100 g (iv) Specific volume=1.5 cm$^3$/g (v) pH at 5% in water=7.5

(vi) Proportion of zinc relative to silica=0.5% by weight

In the following Table I, the different compatibilities of this final product silica with typical constituents of a dentifrice formulation, measured by the tests described above, are reported.

TABLE I

| Ingredients | Fluoride NaF | Pyrophosphate Na/K | Chlorhexidine digluconate | Zinc ZnSO$_4$ |
|---|---|---|---|---|
| % Compatible | 95 | 92 | 75 | 93 |

EXAMPLE 3

Into the reactor used in Example 2, a 6 l base fraction was prepared in the same manner.

When the temperature of 85° C. was attained, the pH of the reaction medium was adjusted to 9 by the addition of sodium silicate solution, 90 g/l. Subsequently, sodium silicate having a concentration in silica of 90 g/l and a SiO$_2$/Na$_2$O ratio of 3.5 was added at a flow rate of 0.090 l/min simultaneously with sulfuric acid at a concentration of 90 g/l, over 20 min. The acid flow rate was adjusted such as to maintain the pH of the medium at a constant value of 9.0.

Two liters of an aqueous solution of sodium sulfate, at a concentration of 64 g/l, were then added, and the simultaneous addition of the sodium silicate and sulfuric acid was continued for 40 min.

The addition of the silicate was then discontinued, but the addition of acid was continued until the pH of the reaction mixture was stabilized at 8.

The medium was then aged for 15 min at this pH and at 85° C.

The pH was then decreased to 4 by the addition of sulfuric acid. Subsequently, the mixture was filtered and the wet filter cake washed with deionized water.

To the disintegrated cake, over 30 min, a solution was added containing 20 g sodium zincate prepared according to Example 1 and 60 g water. The pH was decreased to 8.3 by the addition of 20% sulfuric acid and the reaction mixture was aged for 30 min at 80° C.

The mixture was then filtered and the wet filter cake washed with deionized water until the conductivity of the filtrate was less than 500 microsiemens.

The cake was then disintegrated, then the pH adjusted to 7 by the addition of acetic acid.

A final wash was carried out using deionized water.

The product was then dried by atomization and micronization using a "Jet Pulverizer" type grinder to obtain a particle size of 1.2 microns.

The physicochemical properties of the thickening type silica particulates in the manner were as follows:

(i) BET surface area=220 m$^2$/g (ii) CTAB surface area=200 m$^2$/g (iii) DOP oil uptake=380 ml/100 g (iv) Specific volume=8.0 cm$^3$/g (v) pH at 5% in water=7.5

(vi) Proportion of zinc relative to silica=0.5% by weight.

The respective compatibilities are reported in the following Table II:

TABLE II

| Ingredients | Fluoride NaF | Pyrophosphate Na/K | Chlorhexidine digluconate | Zinc ZnSO$_4$ |
|---|---|---|---|---|
| % Compatible | 95 | 90 | 85 | 98 |

EXAMPLE 4

This example illustrates the formulation of a dentifrice using the silica particulates prepared in Example 2. The proportions were by weight:

(i) Glycerin 22%

(ii) Carboxymethylcellulose 7mFD 1.0%

(iii) Silica 31.5%

(iv) TiO$_2$ 1.0%

(v) ZnSO$_4$.7H$_{2O}$ 0.48%

(vi) Sodium benzoate 0.1%

(vii) Sodium saccharinate 0.2%

(viii) Sodium monofluorophosphate 0.76%

(ix) Sodium fluoride 0.1%

(x) Sodium laurylsulfate, 30% solution in H$_2$O 4.66%

(xi) Aromatic agent (perfume) 0.9%

(xii) Water 37.3%.

This dentifrice composition had satisfactory rheological properties and extruded easily both initially and after storage (2 months). Its antibacterial activity remained even after 2 months of storage at 37° C.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A dentifrice composition comprising a zinc containing dentifrice agent, zinc-compatible precipitated silica particulates and at least one detergent, humectant, perfume, flavorant, therapeutic agent, sweetener, colorant and/or preservative, the zinc-compatible precipitated silica particulates having an effective compatibilizing amount of zinc atoms chemically bonded to surface area sites thereof, a BET surface area ranging from 40 to 600 m$^2$/g, a CTAB surface area ranging from 40 to 400 m$^2$/g, an oil uptake ranging from 80 to 500 cm$^3$/g, and a particle size ranging from 1 to 10 μm.

2. The dentifrice composition as defined by claim 1, said zinc atoms being chemically bonded to the surface area sites thereof via Si—O—Zn covalent bonding.

3. The dentifrice composition as defined by claim 1, the dentifrice agent containing zinc comprising a soluble zinc salt, the particulates being at least 50% compatible with zinc.

4. The dentifrice composition as defined by claim 3, being at least 80% compatible with zinc.

5. The dentifrice composition as defined by claim 4, being at least 95% compatible with zinc.

6. The dentifrice composition as defined by claim 1, the particulates including a maximum mount of 10% by weight of said zinc atoms.

7. The dentifrice composition as defined by claim 6, the particulates including a maximum amount of 5 % by weight of said zinc atoms.

8. The dentifrice composition as defined by claim 7, the particulates including a maximum amount of 1% by weight of said zinc atoms.

9. The dentifrice composition as defined by claim 8, the particulates including a maximum mount of 0.5 % by weight of said zinc atoms.

10. The dentifrice composition as defined by claim 1, the particulates comprising abrasive particles having a BET surface area ranging from 40 to 300 m$^2$/g.

11. The dentifrice composition as defined by claim 10, the particulates having a CTAB surface area ranging from 40 to 100 m$^2$/g.

12. The dentifrice composition as defined by claim 1, the particulates comprising thickening particles having a BET surface area ranging from 120 to 450 m$^2$/g.

13. The dentifrice composition as defined by claim 12, the particulates having a BET surface area ranging from 120 to 300 m$^2$/g.

14. The dentifrice composition as defined by claim 12, the particulates having a CTAB surface area ranging from 120 to 400 m$^2$/g.

15. The dentifrice composition as defined by claim 1, the particulates having an oil uptake ranging from 80 to 500 cm$^3$/g.

16. The dentifrice composition as defined by claim 1, the particulates having a pH ranging from 6 to 10.

17. The dentifrice composition as defined by claim 1, the particulates having an index of refraction ranging from 1.440 to 1.465.

18. The dentifrice composition as defined by claim 1, comprising from 5 % to 35 % by weight of said silica particulates.

19. The dentifrice composition as defined by claim 1, further comprising at least one fluoride, phosphate, polyphosphate, polyphosphonate, pyrophosphate or guanidine.

20. The dentifrice composition as defined by claim 1, comprising from 0.01% to 1% by weight of fluoride atoms.

21. The dentifrice composition as defined by claim 1, further comprising a binder material.

22. The dentifrice composition as defined by claim 1, further comprising a dental abrasive material other than said silica particulates.

23. The dentifrice composition as defined by claim 1, further comprising an anti-plaque agent.

* * * * *